United States Patent [19]

Tamaoki

[11] Patent Number: 5,426,057
[45] Date of Patent: Jun. 20, 1995

[54] METHOD OF MEASURING AMOUNT OF ORGANIC MATERIAL ADSORBED TO SURFACE OF SEMICONDUCTOR SUBSTRATE

[75] Inventor: Makiko Tamaoki, Tokyo, Japan

[73] Assignee: Kabushiki Kaisha Toshiba, Kawasaki, Japan

[21] Appl. No.: 212,862

[22] Filed: Mar. 15, 1994

[30] Foreign Application Priority Data

Mar. 26, 1993 [JP] Japan .................. 5-067221

[51] Int. Cl.6 .................. G01N 33/00; G01N 21/74; H01L 21/306
[52] U.S. Cl. .................. 436/146; 134/902; 436/171; 436/174; 436/177; 156/626.1
[58] Field of Search .................. 134/902; 156/626; 436/146, 171, 177, 178, 174

[56] References Cited

U.S. PATENT DOCUMENTS

| | | | |
|---|---|---|---|
| 4,584,886 | 4/1986 | Matsunaga et al. | 73/863 |
| 4,634,497 | 1/1987 | Shimazaki | 156/646 |
| 4,695,327 | 9/1987 | Grebinski | 134/11 |
| 4,787,997 | 11/1988 | Saito et al. | 156/662 X |
| 4,990,459 | 2/1991 | Maeda et al. | 436/178 |
| 5,248,614 | 9/1993 | Wang | 436/5 |

FOREIGN PATENT DOCUMENTS 60-129136  7/1985  Japan .
2-28533    1/1990  Japan .

OTHER PUBLICATIONS

P. J. Oles et al. *Anal. Chem.* 1974, 46, 2197–2200.
T. Ohmi et al. *J. Electrochem. Soc.* 1993. 140(3), 804–810.

Primary Examiner—James C. Housel
Assistant Examiner—Arlen Soderquist
Attorney, Agent, or Firm—Finnegan, Henderson, Farabow, Garrett & Dunner

[57] ABSTRACT

A method of measuring the amount of organic material adhered to the surface of a semiconductor substrate. In the method, a metal is precipitated by bringing the reaction solution into contact with organic material on the surface of semiconductor substrate. The amount of the organic material adhered to the semiconductor substrate can be determined by detecting the amount of the metal precipitated.

4 Claims, 2 Drawing Sheets

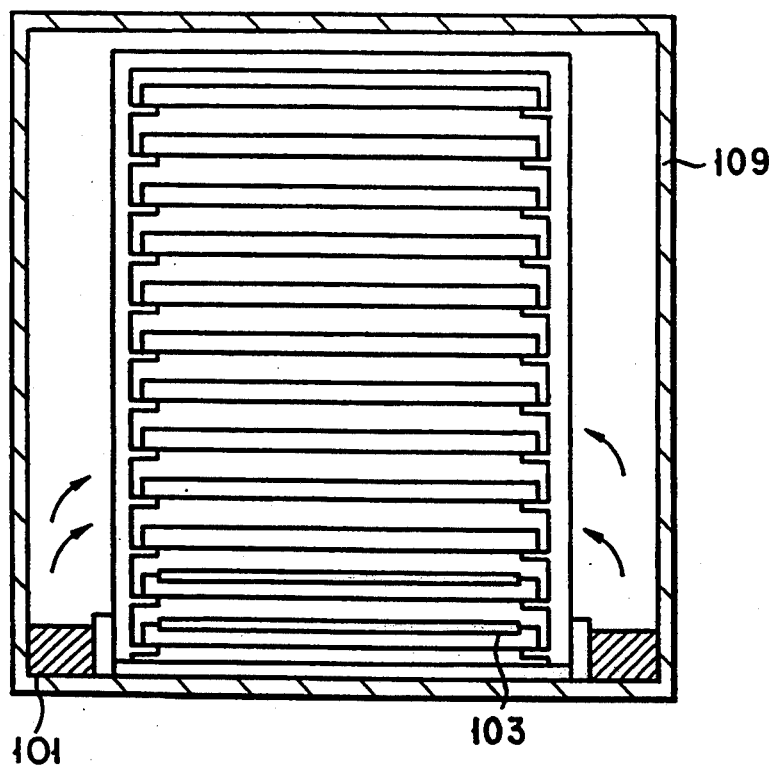
FIG. 4
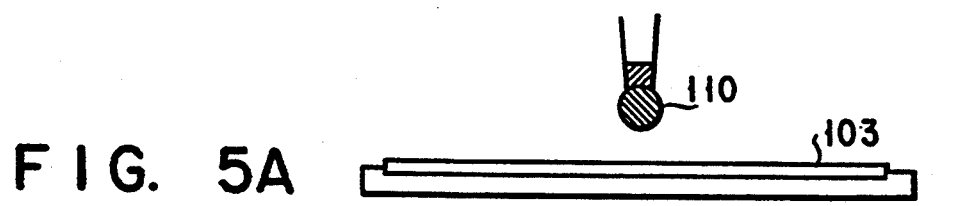
FIG. 5A
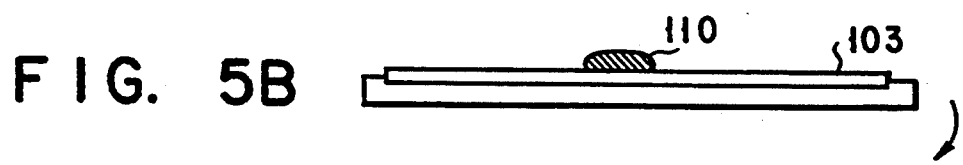
FIG. 5B
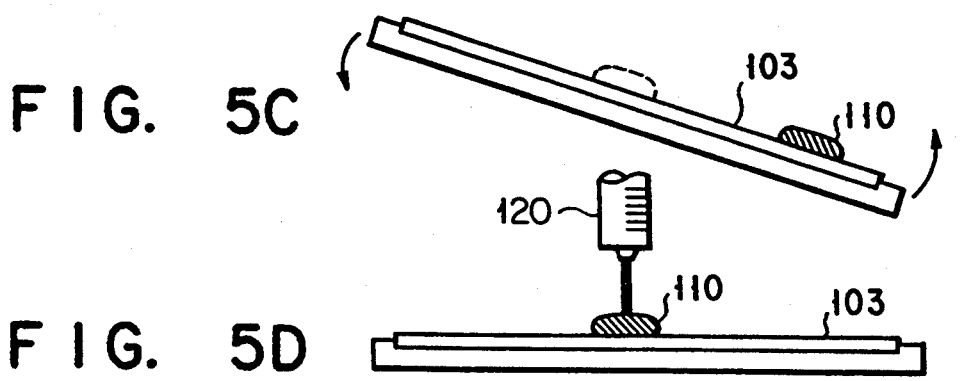
FIG. 5C
FIG. 5D

METHOD OF MEASURING AMOUNT OF ORGANIC MATERIAL ADSORBED TO SURFACE OF SEMICONDUCTOR SUBSTRATE

BACKGROUND OF THE INVENTION

1. Field of the Invention

The present invention relates to a method of measuring an amount of organic material adsorbed to a surface of a semiconductor substrate, which adversely influences the electrical characteristics of the substrate, and which is a factor causing various defects in the product.

2. Description of the Related Art

For the purpose of maintaining a high yield of semiconductors and high reliability of the produced device, it is essential to improve the total cleaning technique. This tendency will be more prominent in the future process technique for downsizing devices and for processing wafers having an larger diameter. In the total cleaning technique for the semiconductor production, it is particularly important to reduce the contamination due to impurities adsorbed to the surface of a semiconductor substrate. If an impurity is adsorbed to a semiconductor, troubles are likely to occur in the steps following the total cleaning. The etching rate and the film being formed may be adversely affected. The electrical characteristics of an insulation film, including the voltage-proof property, may deteriorate.

Not only metal impurities which have been regarded as adversely influencing characteristics of a substrate, but also organic impurities adsorbed to the surface of the substrate. Therefore, the amount of organic material impurities as well as that of metal impurities must be measured in order to determine the amount of impurities to be removed for reducing the influence by contamination.

A conventional method of measuring organic material adsorbed to the surface of a semiconductor substrate, is disclosed in the article "Impurity Removal Method for Semiconductor Surface" in "KOKAI GIHOU (Technical Report Publication 46489×006-1". As can be seen in FIG. 1 of this article, a semiconductor substrate 303, to which organic material is adsorbed, is immersed into tens of milliliters of extrapure water 301 filled in a quartz container 302, and is left to stand for a certain period of time. Thus, the organic material is removed from the semiconductor substrate 303 and dissolved into the extrapure water 301. The solution now containing the organic material is sampled and analyzed by use of a total organic carbon meter (to be called "TOC meter" hereinafter).

As described above, in the conventional method, the semiconductor substrate is immersed into tens of milliliters of extrapure water filled in a quartz container, to remove the organic material from the semiconductor substrate. Obviously, extrapure water is required in a great amount to remove a very small amount of the organic material. Further, the detection sensitivity of the TOC meter is limited to 1 to 2 ppb. Therefore, the smallest amount of organic material (adsorbed to the surface of a semiconductor substrate,) which the TOC meter can detect (hereinafter called "detection limit amount") is $10^{13}$ atoms/cm² in terms of the number of carbons (C) per unit area. More specifically, if the solution is used in an amount of 50 ml, and the TOC meter has a detection limit of 1 ppb, the detection limit amount will be calculated as follows:

$$50 \text{ ml} \times 1 \text{ ppb} = 50 \text{ ml} \times 1 \times 10^{-9} \text{ g/ml} \quad (1)$$
$$= 50 \times 10^{-9} \text{ g}$$

The value obtained by the equation (1) can be converted to the number of carbons (C) by the equation (2):

$$\frac{50 \times 10^{-9} \text{ g}}{12 \text{ g/mol}} \times 6 \times 10^{23} \text{ atoms/mol} = 25 \times 10^{14} \text{ (atoms)} \quad (2)$$

The value obtained by the equation (2) can be converted to the number per unit area of semiconductor substrate, by the equation (3). Since the total surface area (including those of the front and rear surfaces) of a 6-inch substrate is about 350 cm², the number per unit area can be obtained by the following equation (3):

$$\frac{25 \times 10^{14}}{350} - \text{atoms/cm}^2 \approx 1 \times 10^{13} \text{ atoms/cm}^2 \quad (3)$$

Also, in the conventional method described above, organic material is removed from a semiconductor substrate, simply by immersing the semiconductor substrate into extrapure water. Therefore, if the organic material is insoluble to extrapure water, the material cannot not be completely removed. As a result, the efficiency of removal is low, and the sensitivity of the measurement is inevitably low.

A method of measuring a metal impurity adsorbed to the surface of a semiconductor substrate is described, for example, in Jap. Pat. Appln. KOKAI Publication No. 2-28533. In this method, flameless atomic absorption spectrometry is applied for analyzing a metal impurity, and a droplet containing a metal impurity is atomized by heat in, for example, a high-purity graphite carbon furnace (not shown). In the flameless atomic absorption spectrometry, light is emitted from a hollow cathode lamp (not shown) to atomic vapor dissociated due to high temperature in the furnace, and the intensity of the resonant ray absorbed in the atomic vapor is detected. The amount of metal in a droplet can be calculated from the detected intensity. In this metal impurity measuring method, the metal impurity removed from a semiconductor substrate is collected by an acid droplet having a volume of about 0.1 ml. Therefore, the detection limit amount can be in the order of $10^9$ to $10^{10}$ atoms/cm².

As can be understood from the above, the first-mentioned conventional method can measure an amount of organic material, but with a sensitivity 3 to 4 orders of magnitude lower than the second-mentioned conventional method measures an amount of metal impurity.

SUMMARY OF THE INVENTION

The object of the present invention is to provide a method of measuring an amount of organic material, however small it is, adsorbed to the surface of a semiconductor substrate at a high sensitivity.

In order to achieve the object, there is provided a method of measuring an amount of organic material adsorbed to the surface of a semiconductor substrate, comprising the steps of:

bringing a reaction solution containing a metal compound capable of reacting with the organic material into contact with the semiconductor substrate to react the metal compound with the organic material to precipitate a metal on the semiconductor substrate; and calculating an amount (molecule/cm$^2$) of the organic material by measuring an amount (atoms/cm$^2$) of the metal.

With the method of this invention, a very small amount of an organic material can be detected without using a great amount of extrapure water, and the detection sensitivity can be improved.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 4 is a diagram explaining a step which follows the step shown in FIG. 3;

FIG. 5 is a diagram explaining a step which follows the step shown in FIG. 4.

DETAILED DESCRIPTION OF THE PREFERRED EMBODIMENTS

The first embodiment of the present invention will now be described in detail, with reference to FIG. 2 to FIG. 5.

FIG. 2 to FIG. 5 show the outline of a method of measuring the amount of organic material adsorbed to the surface of a semiconductor substrate.

Figure 1:
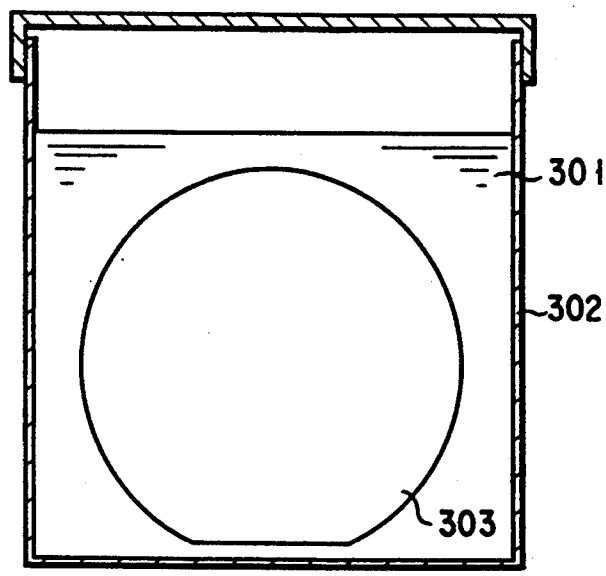
FIG. 1 is a diagram explaining a conventional method of measuring the amount of organic material adsorbed to the surface of a semiconductor substrate.
Figure 2:
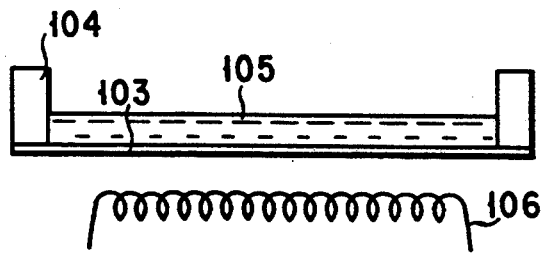
FIG. 2 is a diagram explaining a step of a method according to an embodiment of the present invention, designed for measuring the amount of the organic material adsorbed to the surface of a semiconductor substrate.

As shown in FIG. 2, a semiconductor substrate 103, to which organic material is adsorbed, is fixed to frame 104 at its periphery portions. Then, a reaction solution 105 containing a metal compound, such as selenium oxide (SeO$_2$), which readily be reduced by the organic material is prepared. The reaction solution 105 is applied, using a pipet or the like, dropwise onto the surface of the semiconductor substrate 103 surrounded by the frame 104, wetting the semiconductor substrate 103 and reacting with the organic material. The frame 104 should be made of a material which does not react with the solution 105. In this embodiment, the frame 104 is made of quartz. The frame 104 serves merely to fix the semiconductor substrate 103.

The semiconductor substrate 103 is heated by a heater 106 placed close to the substrate 103, thereby accelerating the reaction between the organic material and the reaction solution 105. The reaction involves the oxidization and reduction specified by the following formulas, in which a metal compound such as SeO$_3$ is reduced to selenium. The heater 106, which is used to accelerate the reaction, can be dispensed with if the reaction fully occurs by itself.

$$2RCH_2OH + SeO_2 \rightarrow 2RCHO + Se + H_2O \quad (4)$$

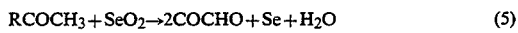

$$RCOCH_3 + SeO_2 \rightarrow 2COCHO + Se + H_2O \quad (5)$$

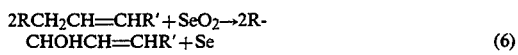

$$2RCH_2CH=CHR' + SeO_2 \rightarrow 2R\text{-}CHOHCH=CHR' + Se \quad (6)$$

where R and R' is each an alkyl group ($-C_nH_{2n+1}$) such as a methyl group, or a benzene ring ($-C_6H_5$), or the like. The formula (4) illustrates a reaction which occurs if the organic material is an alcohol having a hydroxide ($-OH$). The formula (5) represents a reaction which occurs in the case where the organic material is aldehyde, ketone, or carbonic acid, which has a carbonyl group ($-CO$). The formula (6) illustrates a reaction which occurs in the case where the organic material contains a double bond.

The semiconductor substrate 103 is heated as shown in FIG. 2 for a given period of time. Then, the substrate 103, from which the organic material has been removed, is transferred into a water-washing tub 107 filled with extrapure water 101, and is washed in the tub 107. Dissolved in the reaction solution 105, are unreacted materials such as SeO$_2$ and the like, and material other than metal, e.g., Se, formed on the substrate 103. Thereafter, the substrate 103 is washed, and the reaction solution 105 is drained from the tub 107 and discarded. Thus, for example, only Se produced in the reducing reaction by the organic material is precipitated and remains on the surface of the semiconductor substrate 103.

After washed with water and dried, the semiconductor substrate 103 is exposed to hydrofluoric acid (HF) vapor in a sealing device 109 as shown in FIG. 4, rendering the substrate hydrophobic. Then, as can be seen in FIG. 5A and FIG. 5B, about 0.1 ml of dilute hydrofluoric acid solution is applied dropwise onto the semiconductor substrate 103. In the case where the metal formed by the reducing reaction with the organic material is a metal such as Cu, having a low ionization tendency, a mixture solution of acid and oxidizer is applied dropwise onto the semiconductor substrate 103. Next, as shown in FIG. 5C, the semiconductor substrate 103 is inclined, whereby a sample droplet 110 slides down on the surface of the substrate 103. Thus, the metal formed by the reaction between the organic material on the surface of the substrate 103 and the reaction solution 105, and deposited on the semiconductor substrate 103 is collected by the sample droplet 110, which is sucked up by a collecting device 120, as shown in FIG. 5D.

The amount of the metal in the droplet 110 can be determined by means of the flameless atomic absorption spectrometry. In the flameless atomic absorption spectrometry, the droplet is atomized, for example, in a high-purity graphite carbon furnace (not shown), and resonant rays are emitted from a hollow cathode lamp (not shown) to atomic vapor dissociated due to high temperature in the furnace. The intensity of resonant rays absorbed in the atomic vapor is detected, from which the amount of the metal in the droplet 110 is determined.

As expressed by the formulas (1), (2) and (3), the amount of the metal (Se) formed on the substrate 103 by the reduction corresponds to the amount of the organic material adsorbed to the surface of the substrate 103.

Consequently, the amount of organic material adsorbed to the surface of a semiconductor substrate 103 can be calculated from the detected amount of metal formed on the semiconductor substrate 103.

With the flameless atomic absorption spectrometry, since the detection limit amount of a metal such as Se in a solution is 1 ppb, the detection limit amount in terms of the number of atoms per unit area of the semiconductor substrate 103 is expressed by:

$$\frac{1 \text{ (ppb)} \times 10^{-9} \times a \text{ (ml)} \times N_A}{M_{Se} \times b} \text{ atoms/cm}^2 \quad (7)$$

Where
- a: amount of droplet
- b: area of semiconductor substrate ($cm^2$)
- $M_{Se}$: atomic weight of Se
- $N_A$: Abogadro's number When a=0.1 ml, b=175 $cm^2$ (6 inch), the detection limit amount can be obtained by substituting the parameters with these specific numbers, as shown in the following formula (8):

$$\frac{1 \times 10^{-9} \times 0.1 \times 6.02 \times 10^{23}}{78.96 \times 175} \approx 4 \times 10^9 \text{ atoms/cm}^2 \quad (8)$$

Assuming that the organic material which reacted with $SeO_2$ is acetone ($CH_3COCH_3$), the detection limit amount of acetone is $4 \times 10^9$ molecule/$cm^2$, since one molecule of acetone reacts with one molecule of $SeO_2$, and the detection limit amount of Se is $4 \times 10^9$ atoms/$cm^2$. In terms of the number of carbons, the detection limit amount of acetone is $1 \times 10^{10}$ atoms/$cm^2$. In the case of organic material such as unsaturated carbohydrate, two molecules of which react with one molecule of $SeO_2$, the detection limit amount is $8 \times 10^9$ molecules/$cm^2$. If the organic material is methanol ($CH_3OH$), the detection limit amount in terms of the number of carbons is $2 \times 10^{10}$ atoms/$cm^2$.

In other words, with the present invention, the measurement sensitivity is as high in the order of $10^{10}$ atoms/$cm^2$ for the organic material adsorbed to the substrate 103.

The amount of the collected droplet containing the metal is sufficient for the flameless atomic spectrometry. Further, the droplet need not be concentrated for the spectrometry. Therefore, the amount of the metal can be determined directly, not influenced by impurities present in the atmosphere.

The second embodiment of the present invention will now be described in detail with reference to FIG. 6.

The components identical to those used in the first embodiment are designated by the same reference numerals, and will not be described in detail.

In the first embodiment, the reaction takes place automatically, simply by applying the reaction solution containing the metal compound onto the organic material formed on the surface of the semiconductor substrate. The application of the solution onto the material, however, does not suffice to make the organic material, e.g., a chain carbohydrate having a low reducibility, readily react with the metal compound. The second embodiment has been made of solve this problem, and provides a method in which an organic material can easily react with a metal compound.

Figure 6:
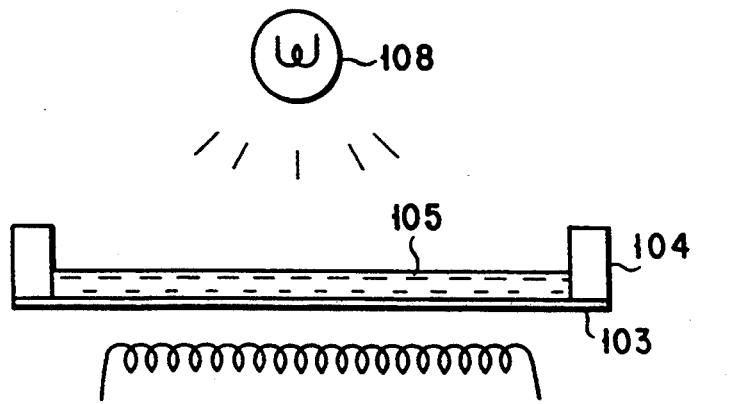
FIG. 6 is a diagram explaining a step of a method according to another embodiment of the present invention, designed for measuring the amount of the organic material adsorbed to the surface of a semiconductor substrate.

As shown in FIG. 6, a semiconductor substrate 103 to which organic material is adsorbed is fixed to frame 104 at its periphery portions. Then, a reaction solution 105 containing a metal compound such as silver nitrate ($AgNO_3$) which can react with the organic material is applied dropwise onto the surface of the semiconductor substrate 103 surrounded by the frame 104, wetting the semiconductor substrate 103.

Then, light is applied from a UV (ultraviolet) lamp 108 or the like onto the surface of the semiconductor substrate 103, thus accelerating the reaction between the metal compound and the organic material. $AgNO_3$ reacts with a reducing organic material, such as aldehyde, to be reduced to silver. A chain carbohydrate having a low reducibility is photooxidated by the UV irradiation and thereby rendered a reducing organic material. Then, the reducing organic material reacts with $AgNO_3$.

Figure 3:
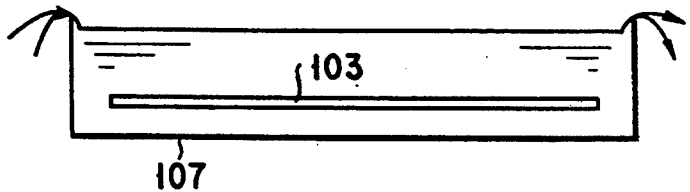
FIG. 3 is a diagram explaining a step which follows the step shown in FIG. 2.

After a given period of time, the semiconductor substrate 103 is washed with water as shown in FIG. 3. The materials remaining unreacted in the solution 105, and the materials, other than metals, formed on the semiconductor substrate 103 by the reaction with the organic material are thereby discarded.

After washed with water and dried, the semiconductor substrate 103 is exposed to hydrofluoric acid (HF) vapor in a sealing device 109 as shown in FIG. 4, rendering the substrate hydrophobic. Then, as can be seen in FIG. 5A and FIG. 5B, about 0.1 ml of dilute hydrofluoric acid solution is applied dropwise onto the semiconductor substrate 103. In the case where the metal formed by the reducing reaction with the organic material is a metal, such as Cu, having a low ionization tendency, a mixture solution of acid and oxidizer is applied dropwise onto the semiconductor substrate 103. Next, as shown in FIG. 5C, the substrate 103 is inclined, whereby a sample droplet 110 slides down on the surface of the substrate 103. Thus, the metal formed by the reaction between the organic material on the surface of the substrate 103 and the reaction solution 105, and deposited on the semiconductor substrate 103, is collected by the sample droplet 110, which is sucked up by a collecting device 120, as shown in FIG. 5D.

The amount of the metal in the droplet 110 can be determined by means of flameless atomic absorption spectrometry. The amount of organic material on the surface of a semiconductor substrate 103 can be calculated from the measured amount of metal formed on the substrate 103.

In the second embodiment, unreactive organic material is converted to a reactive one by photoreaction, and then made to react with a metal compound. Therefore, the sensitivity of the measurement of the organic material can be improved.

Additional advantages and modifications will readily occur to those skilled in the art. Therefore, the invention in its broader aspects is not limited to the specific details, and illustrated examples shown and described herein. Accordingly, various modifications may be made without departing from the spirit or scope of the general inventive concept as defined by the appended claims and their equivalents.

What is claimed is:

1. A method of measuring an amount of an organic material adsorbed to the surface of a semiconductor substrate, comprising the steps of:
   preparing a reaction solution containing an inorganic compound capable of reacting with the organic material adsorbed to the surface of the semiconductor substrate and forming a precipitate;

reacting a reaction solution containing the inorganic compound with the organic material on the substrate to form a precipitate;

dissolving and quantifying the precipitate in the reaction solution; and calculating an amount (molecules/cm$^2$) of the organic material present on the substrate from the quantity (atoms/cm$^2$) of the precipitate.

2. The method according to claim 1, further comprising the step of accelerating a reaction between said organic material and said reaction solution.

3. The method according to claim 2, wherein said step of accelerating said reaction is heating said semiconductor substrate.

4. The method according to claim 2, wherein said step of accelerating said reaction is irradiating light on said semiconductor substrate.

* * * * *